United States Patent
Maier

(10) Patent No.: US 8,333,685 B2
(45) Date of Patent: Dec. 18, 2012

(54) SYSTEM AND METHOD FOR IMAGE-GUIDED THERAPY PLANNING AND PROCEDURE

(75) Inventor: Cynthia Maier, Delafield, WI (US)

(73) Assignee: Hologic, Inc., Marlborough, MA (US)

( * ) Notice: Subject to any disclaimer, the term of this patent is extended or adjusted under 35 U.S.C. 154(b) by 804 days.

(21) Appl. No.: 12/402,311

(22) Filed: Mar. 11, 2009

(65) Prior Publication Data

US 2009/0234175 A1  Sep. 17, 2009

Related U.S. Application Data

(60) Provisional application No. 61/035,630, filed on Mar. 11, 2008.

(51) Int. Cl.
*A61M 36/00* (2006.01)
*A61M 36/04* (2006.01)

(52) U.S. Cl. ............................... 600/3; 600/1

(58) Field of Classification Search ............ 600/1–8; 424/1.11–1.89; 378/64–69
See application file for complete search history.

(56) References Cited

U.S. PATENT DOCUMENTS

| | | | |
|---|---|---|---|
| 6,095,975 A * | 8/2000 | Silvern | 600/439 |
| 6,792,073 B2 * | 9/2004 | Deasy et al. | 378/65 |
| 7,155,043 B2 | 12/2006 | Daw | |
| 7,176,683 B2 | 2/2007 | Pineda | |
| 2006/0259282 A1 * | 11/2006 | Failla et al. | 703/2 |

OTHER PUBLICATIONS

Update of AAPM Task Group No. 43 Report: A revised AAPM protocol for brachytherapy does calculations; Med. Phys. vol. 31 No. 3, Mar. 2004; pp. 633-674.

Supplement to the 2004 update of the AAPM Task Group No. 43 Report; Med. Phys. vol. 34 No. 6, Jun. 2007; pp. 2187-2206.

Erratum: "Update of AAPM Task Group No. 43 Report: A revised AAPM protocol for brachytherapy dose calculations" [Med. Phys. 31, 633-674 (2004)].

* cited by examiner

*Primary Examiner* — Charles A Marmor, II
*Assistant Examiner* — Catherine E Burk
(74) *Attorney, Agent, or Firm* — Lando & Anastasi, LLP

(57) ABSTRACT

A method for generating a treatment plan for therapy comprising obtaining image data representing a tissue, determining a therapy dose map comprising dose values for a plurality of dose points based on the image data, forming a desired dose value vector comprising the dose values for the plurality of dose points, determining a one or more potential therapy locations based on the image data, determining a therapy dose map equation for each of the plurality of dose points based on the one or more potential therapy locations, forming a matrix based on the therapy dose map equations for the each dose points, determining an inverse of the matrix and determining the treatment plan by multiplying the desired dose value vector by the inverse of the matrix.

21 Claims, 3 Drawing Sheets

SYSTEM AND METHOD FOR IMAGE-GUIDED THERAPY PLANNING AND PROCEDURE

This application claims the benefit of U.S. Provisional Application No. 61/035,630, filed Mar. 11, 2008, the contents of which are hereby incorporated by reference.

TECHNICAL FIELD

The present invention relates to therapy planning, in particular to a method and system for therapy planning using medical image data.

SUMMARY OF THE INVENTION

In certain medical procedures, a treatment device can be placed in tissue of a patient for providing a therapeutic effect. The placement of such a device can be permanent or transient, depending on the therapy planned. For example, a device can be placed at a therapy location for a certain period of time, and then removed from the tissue being treated.

In the conduct of planning and executing such a procedure, it tends to be advantageous to be able to plan out, and/or refine placement of treatment devices in a tissue. Such planning can account for and adjust multiple factors, such as the tissue being treated, proximity of such tissue to other sensitive tissue or organs of the body, the device and dosage strength of the device, the dwell time of the device in the tissue to be treated, blood vessels and blood flow. It can also tend to be advantageous to, based on a determined therapy plan, provide guidance information to a user performing the procedure so as to assist the user in directing the treatment device or devices to the planned therapy location(s). In some instances, it can also tend to be advantageous to provide automated guidance of the device(s) to the therapy locations.

For example, brachytherapy is a form of radiation therapy that places radioactive sources, or "seeds", in or near a targeted tissue with destruction of the targeted tissue as the goal. In the example of brachytherapy, a treatment device may be a brachytherapy seed and a therapy location may be referred to as a seed location. For prostate brachytherapy, for example, there are two currently accepted methods: permanent seed implantation and high dose rate (HDR) temporary brachytherapy. Permanent seed implantation involves injecting approximately 100 radioactive seeds into the prostate gland. These seeds give off their radiation at a low dose rate over several weeks or months, and the seeds themselves remain in the prostate gland permanently. HDR temporary brachytherapy instead involves surgical placement of narrow plastic catheters into the prostate gland through the perineum, such that one end of each catheter is in the prostate gland and the other end of each catheter is accessible outside the perineum. A computer-controlled machine pushes a single highly radioactive seed into the catheters one by one, controlling the length of time the seed stays at each of multiple seed locations along each catheter. After the treatment, the catheters are then pulled out, and no radioactive material is left in the prostate gland. By controlling how long each single seed remains at each seed location (i.e., the "dwell time"), the radiation dose is varied over the prostate in order to target high-risk areas, and to avoid vital structures such as the urethra and the rectum.

For both types of brachytherapy, a treatment plan is generated by a computer using previously acquired medical images of the organ to be treated. These images may be ultrasound images, computed tomography (CT) images or magnetic resonance (MR) images. For permanent seed brachytherapy, a plan for seed placement locations is generated by a radiation oncologist or radiation physicist targeting the radiation dose to the tissues that are to be destroyed, sparing adjacent normal tissue or vital anatomy. For HDR brachytherapy, the location of the catheters and therefore the possible seed locations are known, and dwell times for each possible seed location may be calculated in order to generate an appropriate treatment plan.

Certain brachytherapy planning is accomplished using "forward planning" by iteratively adjusting an organ-specific template for either seed locations (permanent seed brachytherapy) or dwell times (HDR brachytherapy) in a computer based treatment planning tool. These parameters are adjusted and a resulting therapy dose map is calculated until a satisfactory therapy dose map, i.e., a therapy dose map that treats the target tissue and avoids the vital surrounding structures, is achieved.

Inverse planning algorithms can also be used to instead start with a desired dose distribution and calculate an appropriate seed placement plan (for permanent seed brachytherapy) or dwell time plan (for HDR brachytherapy). For these algorithms, a physician or physicist examines a series of images of the targeted tissue and uses treatment planning software to define a desired therapy dose map, usually displayed as dose isocontours on a background image. In some prior art systems, inverse planning algorithms then formulate an optimization problem to find a desirable solution for the seed placements or dwell times. These algorithms first define an objective function from the desired dose distribution. The difference between the actual dose that would be delivered by a treatment plan to a dose point i and the desired dose at that point is converted into a penalty value $W_i$. A cost function is formed from the sum of the $W_i$ over all dose points i in the treatment volume. The penalty value increases with the difference between the actual dose at a point for a given solution and the desired value. A solution for seed placements or dwell times is calculated by finding the treatment plan that minimizes the cost function from among the group of all possible treatment plans. Various optimization algorithms have been proposed for solving this problem, including a simulated annealing algorithm which is statistically guaranteed to find a global minimum in the solution space. However, these optimization approaches require the use of somewhat arbitrary schemes to convert a desired therapy dose map into a cost function. In addition, most optimization approaches are not guaranteed to find a solution that will correspond to a global minimum for the cost function. The simulated annealing algorithm, while proven to be capable of producing clinically acceptable treatment plans with a reasonable computation time requires careful tuning for each specific clinical task.

These treatment techniques described above for brachytherapy require treatment planning based on accurate needle or catheter positioning by way of imaging guidance for anticipated dose delivery, detection of needle or catheter, and recalculation of dose based on actual catheter placement.

For most treatments, such as brachytherapy, it would be advantageous to provide computation of the recalculated dose within a short time frame, for example under one hour. Such a re-calculation, or re-generation of a treatment plan and provision of guidance information associated therewith, tend to be advantageous in the provision of treatment planning.

In an aspect of the invention a method is provided for generating a treatment plan for therapy, comprising: obtaining image data representing a tissue; determining a therapy dose map comprising dose values for a plurality of dose points based on the image data; forming a desired dose value vector comprising the dose values for the plurality of dose points; determining a one or more potential therapy locations based on the image data; determining a therapy dose map equation for each of the plurality of dose points based on the one or more potential therapy locations; forming a matrix based on the therapy dose map equations for the each dose points; determining an inverse of the matrix; and determining the treatment plan by multiplying the desired dose value vector by the inverse of the matrix.

The treatment plan may be a vector representing a one or more determined therapy locations. Based on the treatment plan, one or more treatment devices, each corresponding to the one more determined therapy locations, may be injected into the tissue to the each determined therapy location. The treatment plan may be for brachytherapy and the one or more treatment devices may each be brachytherapy seeds. The resulting treatment plan vector may represent the one or more determined brachytherapy seed locations multiplied by a dwell time associated with the each determined brachytherapy seed location.

Each therapy dose map equation may be determined by summing dose values from the one or more potential therapy locations at the each dose points. The matrix may be an M×N matrix where M is equal to the number of dose points in the plurality of dose points and N is equal to the number of potential therapy locations. The determining of the brachytherapy treatment plan may include generation of a second therapy dose map from the one or more determined therapy locations. At least one of the one or more determined therapy locations or the dwell time associated with the each determined therapy location may be adjusted to determine a further therapy dose map.

In another aspect of the invention, a computer media product is provided, comprising a computer usable medium having a computer readable code embodied therein, the computer readable code being readable by a computer processor of a computer system to cause the system to: obtain image data representing a tissue; determine a therapy dose map comprising dose values for a plurality of dose points based on the image data; form a desired dose value vector comprising the dose values for the plurality of dose points; determine a one or more potential therapy locations based on the image data; determine a therapy dose map equation for each of the plurality of dose points based on the one or more potential therapy locations; form a matrix based on the therapy dose map equations for the each dose points; determine an inverse of the matrix; and determine the treatment plan by multiplying the desired dose value vector by the inverse of the matrix.

The treatment plan may be a vector representing a one or more determined therapy locations. Based on the treatment plan, one or more treatment devices, each corresponding to the one more determined therapy locations, may be injected into the tissue to the each determined therapy location. The treatment plan may be for brachytherapy and the one or more treatment devices may each be brachytherapy seeds. The resulting treatment plan vector may represent the one or more determined brachytherapy seed locations multiplied by a dwell time associated with the each determined seed location.

The each therapy dose map equation may be determined by summing dose values from the one or more potential therapy locations at the each dose points. The matrix may be an M×N matrix where M is equal to the number of dose points in the plurality of dose points and N is equal to the number of potential therapy locations. The determining of the brachytherapy treatment plan may include generation of a second therapy dose map from the one or more determined brachytherapy seed locations. At least one of the one or more determined therapy locations or the dwell time associated with the each determined therapy location may be adjusted to determine a further therapy dose map.

In a further aspect of the invention a plan generation system is provided for generating a treatment plan, comprising: a medical image storage medium for storing imaging data; a treatment planning storage medium for storing treatment planning data; a treatment planning system in communication with the medical image storage medium and treatment planning storage medium, the planning system obtaining the imaging data from the medical image storage medium and obtaining the treatment planning data from the treatment planning storage medium for analysis by a processor of the planning system, the processor: determining a therapy dose map comprising dose values for a plurality of dose points based on the imaging data received from the medical image storage medium, forming a desired dose value vector comprising the dose values for the plurality of dose points, determining a one or more potential therapy locations based on the image data received from the medical image storage medium, determining a therapy dose map equation for each of the plurality of dose points based on the one or more potential therapy locations, forming a matrix based on the therapy dose map equations for the each dose points, determining an inverse of the matrix, determining the treatment plan by multiplying the desired dose value vector by the inverse of the matrix; displaying the treatment plan to a display device to guide a user in injecting one or more treatment devices, each corresponding to the one more determined therapy locations, into the tissue to the each therapy location based on the treatment plan.

The treatment plan may be a vector representing a one or more determined therapy locations; represents the one or more determined therapy locations multiplied by a dwell time associated with the each determined therapy location; the each therapy dose map equation may be determined by summing dose values from the one or more potential therapy locations at the each dose points; and the matrix may be an M×N matrix where M is equal to the number of dose points in the plurality of dose points and N is equal to the number of potential therapy locations. The treatment device may be a brachytherapy seed.

BRIEF DESCRIPTION OF THE DRAWINGS

Embodiments are illustrated by way of example and not limitation in the figures of the accompanying drawings, in which like reference numerals indicate corresponding, analogous or similar elements, and in which.

Figure 1:
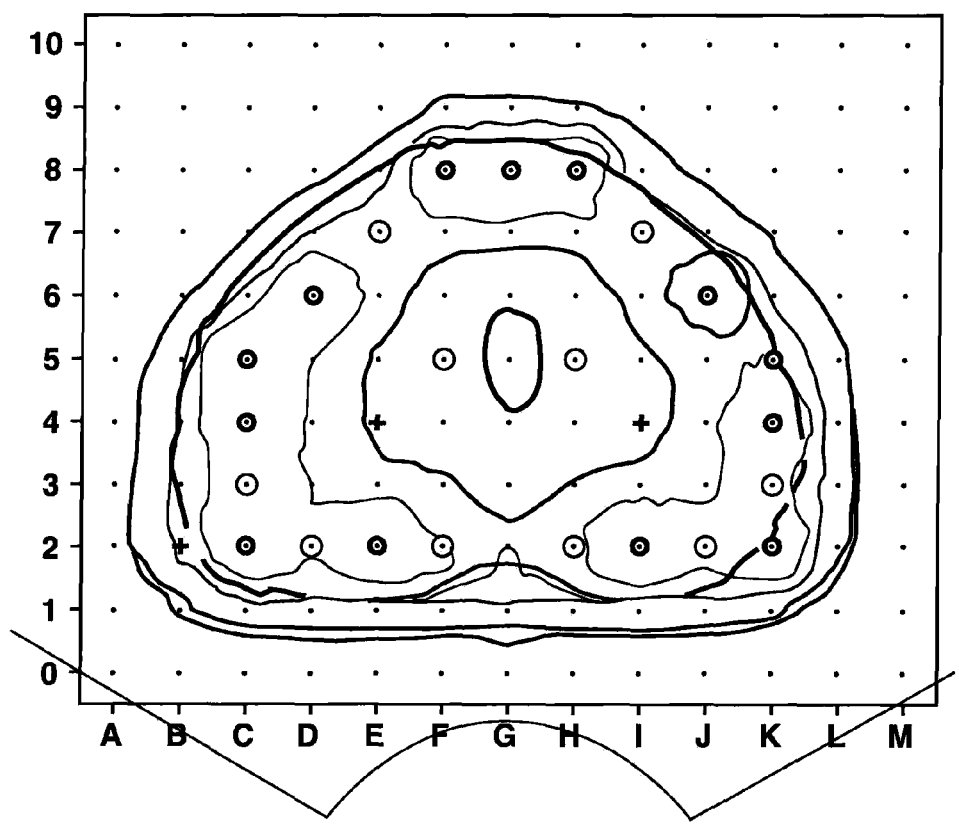
FIG. 1 shows a determined therapy dose map on an ultrasound image for prostate brachytherapy planning. Potential locations for seed placement are shown as a grid of points, and determined seed locations included in the treatment plan are shown as circled grid points.

It will be appreciated that for simplicity and clarity of illustration, elements shown in the figures have not necessarily been drawn to scale. For example, the dimensions of some of the elements may be exaggerated relative to other elements for clarity.

DETAILED DESCRIPTION

In the following detailed description, numerous specific details are set forth in order to provide a thorough understanding of embodiments. However it will be understood by those of ordinary skill in the art that the embodiments may be practiced without these specific details. In other instances, well-known methods, procedures, components and circuits have not been described in detail so as not to obscure the embodiments.

In certain medical procedures, a treatment device can be placed in tissue of a patient for providing a therapeutic effect. The placement of such a device can be permanent or transient, depending on the therapy planned. For example, a device can be placed at a therapy location for a certain period of time, and then removed from the tissue being treated. For other treatments, such as RF or cryogenic ablation, the device power can be independently controlled. For these treatments, the device can be placed at a certain location and turned on and off as required throughout the procedure.

In embodiments for treatment planning, medical images of the tissue to be treated are first obtained. These images may be examined in a treatment planning system and/or software, possibly in conjunction with the input by a user (i.e., a physician or radiation physicist) to create a treatment plan. A desirable treatment plan that tends to correspond delivery of a treatment device can then be devised, taking into account factors such as the tissue being treated, proximity of such tissue to other sensitive tissue or organs of the body, the device and dosage strength of the device, and the dwell time or treatment duration and power of the device in the tissue to be treated. Based on a determined therapy plan, embodiments can also provide guidance information to a user performing the procedure so as to assist the user in directing the treatment device or devices to the planned therapy location(s). In some instances, it can also tend to be advantageous to provide automated guidance of the device(s) to the therapy locations.

The therapy plans can include a therapy dose map, which provides the location for placement of the device(s) in tissue. A desired therapy dose map may be inputted by a user, and in some embodiments, treatment planning systems and/or software may be used to determine a desired therapy dose map. Based on a desired therapy dose map, treatment planning systems and software may determine a treatment plan and a determined dosage map. The user may approve the determined treatment plan and determined therapy dose map, or make iterative adjustments until a satisfactory treatment plan and satisfactory therapy dose map is obtained from the system.

For example, in brachytherapy treatment, a treatment plan can relate to delivery of adequate radiation dosage to a treatment target volume and sparing of neighbouring vital structures. Similarly, for RF (or cryogenic) ablation the treatment plan can relate to the adequate distribution of heat (or cold) to a treatment target volume while sparing neighbouring vital structures. In the example of brachytherapy treatment the treatment device may tend to be referred to as a brachytherapy seed and the therapy location may tend to be referred to as a seed location.

FIG. 1 shows an embodiment relating to brachytherapy of a determined therapy dose map for a determined treatment plan during prostate permanent seed brachytherapy planning. In this case, an ultrasound image may be used to plan the treatment. Potential locations for seed placement may be shown as a grid of points overlaid on the ultrasound image of the prostate and determined seed locations may be shown on the determined treatment as circled grid points. These locations for seed placement may be potential locations for seed placement because while it may be possible for a seed to be physically placed at such a location, the determined treatment plan may find that a seed may not be required at such a location. Dose isocontours determined based on these determined seed locations may be displayed overlaying the image as well. A three-dimensional map of the prostate may be built up from a stack of such two-dimensional images (such as FIG. 1) in order to determine a three-dimensional determined therapy dose map which may include determined locations for seed placement. Planning may be done before an actual treatment application using previously acquired images, and/or information obtained during the treatment procedure, such as additional imaging of the tissue (to determine treatment volume changes or movement of tissue of interest), the position of catheters (deviation of anticipate path), treatment seeds, or the position of critical structures, so an update to the plan can be performed during the procedure.

An initial therapy dose map can be generated in a number of ways. For example, a predetermined or saved template of potential locations for seed placements for the tissue of interest may be used. In an embodiment where seed brachytherapy of the prostate is permanent, a "prostate template" with a desired therapy dose map for an average-sized prostate gland may be saved between patients, then retrieved and modified for each individual patient. Alternatively, methods may provide a therapy dose map that is determined automatically from medical images using software methods that identify anatomy to be spared and define regions for targeting. For example, MR imaging may be used to create a stack of images of a prostate that is to be treated with brachytherapy. Software routines that identify the capsule of the prostate, the rectum, the seminal vesicles and the urethra may be used to create an appropriate therapy dose map for that individual and the tissue of interest. Regions defined as having a higher likelihood of cancer may be specifically targeted for a boosted dose rate. These software routines may warp stored template images to the individual's prostate images to identify these structures, or they may use the pixel intensity values in the MR images to identify these structures. Clustering methods using measured MR parameters such as tissue, apparent diffusion coefficient, and parameters related to contrast agent uptake may be used to delineate areas of increased likelihood of cancer. A combination of both these approaches may be used in certain embodiments.

A determined therapy dose map for a distribution of brachytherapy seeds may be expressed as a sum of a series of individual therapy dose maps, each of which individual therapy dose maps may correspond to an individual seed placement at a different location. The individual therapy dose map for each of these individual seeds may differ only by having its center shifted to a location corresponding to a potential location for seed placement. The determined therapy dose map corresponding to a determined treatment plan may be obtained by summing these individual therapy dose maps where, for HDR brachytherapy, each individual therapy dose map is multiplied by the dwell times corresponding to the seed at a determined location prior to summing. The individual therapy dose map for an individual brachytherapy seed may be calculated using the AAPM task group 43 formalism (see, for example, Rivard M. J., Coursey B. M., DeWerd L. A., Hanson W. F., Huq M. S., Ibbott G. S., Mitch M. G., Nath R., Williamson J. F., "Update of AAPM Task Group No. 43 Report: A revised AAPM protocol for brachytherapy dose calculations." Med Phys 31:633-674; 2004, all hereby incorporated by reference). These individual therapy dose maps may be calculated on a grid of dose points once per treatment planning session, and then stored as a look-up table to speed later calculations of the treatment plan. The grid of dose points may have a spacing corresponding to the volume pixel ("voxel") size in the treatment-planning images. The total dose $D_i$ delivered to a dose point i (i.e., at the ith voxel) from all seeds may be calculated from this look-up table and the set of seed positions $P_j$ (where j labels the seed) given by a particular treatment plan.

The potential locations of seed placement may be the set of voxels in the treatment-planning images. This set of voxels may be limited to voxels inside of a specified tissue treatment volume, as it may be desirable to limit seed placement to this region or alternatively, it can be the entirety of a tissue or individual. In addition, voxels inside areas that are to be spared radiation may also be excluded from the set of voxels corresponding to potential seed positions. All other voxels inside the treatment volume are sites for potential seed placement, and j ranges over these voxels. In an alternative embodiment the potential locations of seed placement may be predefined in a saved template of potential locations of seed placement, or may be predefined based on the location of instruments capable of delivering a brachytherapy seed previously inserted into tissue, such as a catheter in for example, HDR brachytherapy.

A series of equations may be written wherein each individual equation corresponds to an individual dose point in the tissue being treated. An individual dose point may correspond to an individual voxel in the treatment-planning images. For example, if MR reference images are used for planning, and a stack of 10 axial images with 256×256 displayed resolution covers the entire prostate and surrounding area, there will be 10×256×256=655,360 voxels and thus there may be 655,360 dose points. An equation for a dose point may be determined relating a desired dose value to a sum of doses from each potential location of a seed. As an example, it tends to be common practice in the field that a desired dose contour can be traced onto the images in the image data, indicating areas which need to achieve a desired dosage, as well as areas that need to remain below a certain dosage. Desired dosages can be set by a skilled person based on the therapeutic effect sought, and/or with reference to dosage guidelines. Equations may be determined for each dose point in the image data set. Alternatively, a reduced matrix size may be used via an interpolation method if the voxel size is sufficiently smaller than the scale of the spatial variations in the therapy dose map, or a reduced region size for therapy dose map calculation may be specified. A reduced matrix size where each voxel corresponds to the minimum spacing allowed between seeds may be used. Thus, in an exemplary embodiment, a total of M individual dose points may be labeled by the index i.

The total dose resulting from all implanted seeds for each dose point may be calculated by: $D_i=\text{Sum}_j(d_j)$ where j ranges over all the determined N seed locations. A series of M linear equations each corresponding to a single dose point i may be determined. In an embodiment each of these linear equations may sum to the desired dosage at each dose point based on the sum of the dose value resulting from each potential location for seed placement multiplied by the dwell time for each seed prior to summing. The treatment plan may be determined by determining the desired dwell time for each potential location for seed placement. A determination of a dwell time of zero for a potential location for seed placement may be indicative of a seed not being necessary at a potential location for seed placement in the treatment plan. Typically, there will be more equations than there are variables to solve for, i.e., the problem is over-determined. These equations may be expressed in matrix form as:

$d \times t = D$, where d is a M×N matrix constructed from the coefficients of the series of linear equations corresponding to a single dose point i, as described above;

vector t may be a N×1 vector, and may represent the resultant treatment plan, containing either a one or zero according to the presence of a seed at each potential location for a seed placement multiplied by a dwell time; and vector D may be a 1×M vector which may contain the desired dose values for each dose point.

To determine the treatment plan the inverse of matrix d may be determined, such as the Moore-Penrose pseudo inverse of the matrix, typically by using a Singular Value Decomposition (SVD). Multiplying this pseudo inverse by vector D gives a least-squares solution for vector t, the resulting treatment plan vector. Matrix regularization methods such as the method of Tikhonov may be used in the case of an ill-conditioned matrix to remove singular values at the expense of some accuracy.

The determined treatment plan may have a corresponding determined therapy dose map. The user of the treatment planning system may approve the determined treatment plan and corresponding determined therapy dose map, or make iterative adjustments to, for example, seed locations and/or dwell times, wherein the methods of the present invention may determine a satisfactory therapy dose map and corresponding satisfactory treatment plan.

An accepted, approved and/or generated treatment plan can then be used to guide a brachytherapy treatment procedure, such as by directing one or more brachytherapy seeds to a determined location of seed placement, such as for example, a voxel in the image data representing tissue for treatment, in accordance with the therapy dose map and treatment plan. As described above, the placement of seeds above can be by way of a catheter in permanent or HDR treatment procedures. In some embodiments, once the treatment plan and therapy dose map has been generated and approved, data representations of such can be provided to a catheter guidance system that assists a user in directing the catheter to place the seeds at the desired locations of seed placement. Such guidance systems may operate by receiving data representation of the plan, therapy dose map, and target tissue, which can generate a display to guide the user or guide the catheter or treatment device in an automated manner.

Figure 2:
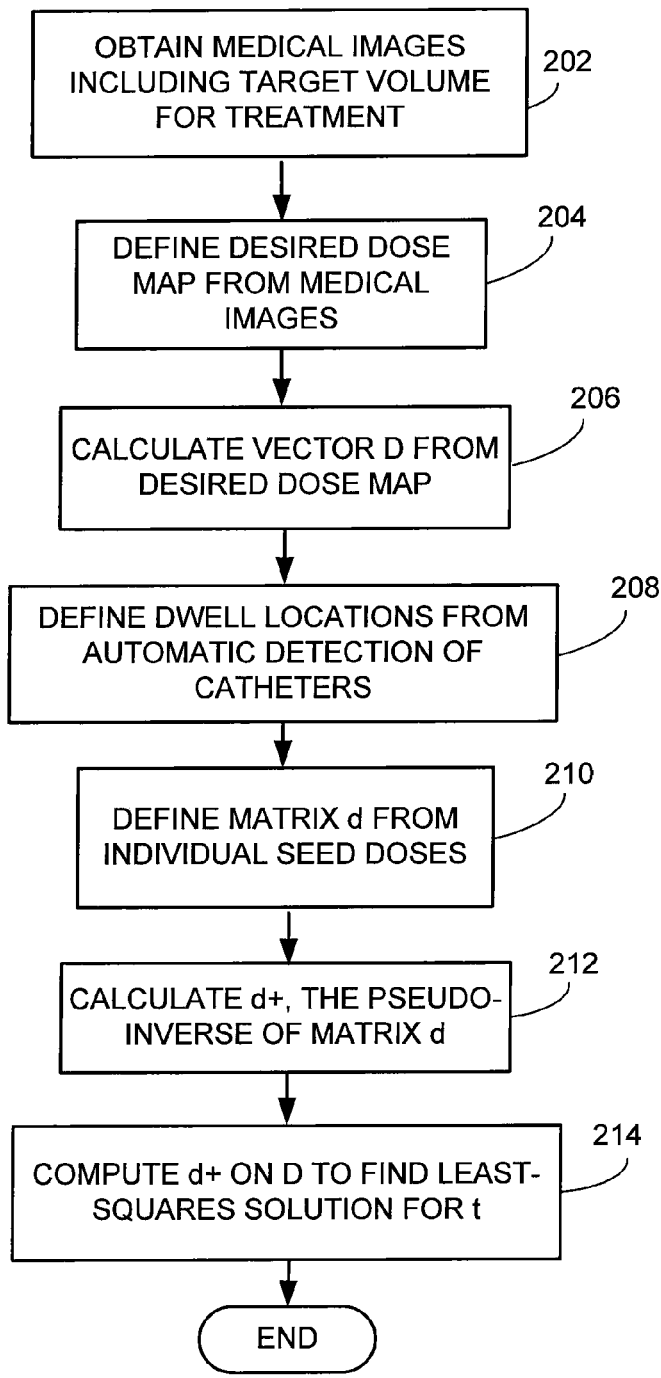
FIG. 2 shows a flowchart of an embodiment of a method for determining a brachytherapy treatment plan in accordance with an aspect of the invention.

FIG. 2 shows a flowchart of an embodiment of a method for HDR brachytherapy treatment planning in accordance with aspects of the invention, such as described in detail above.

At Block 202, medical images of an area of the body may be obtained for brachytherapy treatment planning. These images may be MRI images, CT images, ultrasound images, or any other medical imaging modality.

At Block 204, a user may determine a therapy dose map corresponding to the anatomy depicted in the medical images. Alternatively, a therapy dose map may be calculated automatically from the medical images obtained at 202 by a computer based system and software.

At Block 206, a vector D may be formed from the desired dose values determined from all the dose points in the therapy dose map. In some embodiments, each dose point may correspond to a single voxel in the medical image.

At Block 208, in this embodiment, the locations of previously inserted catheters may be determined using computer based system and software as is well known in the art. Such positions may determine potential locations for seed placement.

At Block 210, a matrix d is determined with rows corresponding to the individual contributions of each potential individual seed to the desired dose value at each dose point. The individual contributions of each potential individual seed at each dose point may be determined using methods as described above.

At Block 212, the pseudo-inverse of matrix d is determined, for example, using a SVD approach and possibly with matrix regularization.

At Block 214, the treatment plan is determined by determining the approximate least-squares solution for vector t, the resulting treatment plan, by multiplying vector D by the pseudo-inverse of matrix d. Values in vector D may correspond to a value of one if, a seed is present at the potential location for seed placement, or a value of zero, if no seed is present, multiplied by the dwell time for potential location for seed placement.

Figure 3:
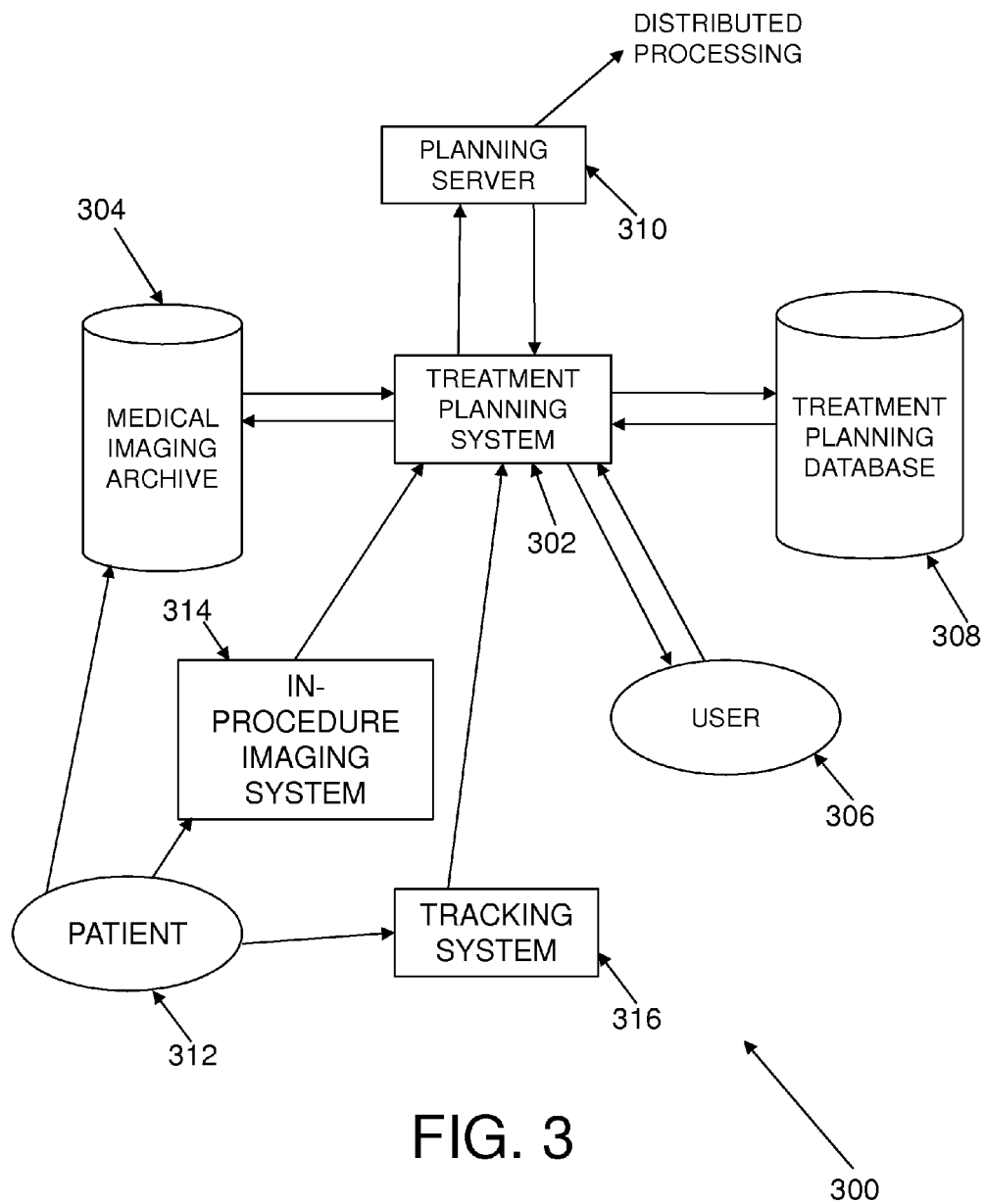
FIG. 3 shows an embodiment of a system for determining a brachytherapy treatment plan in accordance with an aspect of the invention.

With reference to FIG. 3, an embodiment of the disclosed invention is presented in the context of a treatment planning system for determining a brachytherapy treatment plan 300 in accordance with an aspect of the invention. The system may include computer programming for using a computer processor to perform aspects of brachytherapy treatment planning system 302. This system may operate on a computing system which may include a central processor, secondary processors, memory, input devices, such as a keyboard, mouse or display, and output devices such as an LCD display. This system may import medical images from a medical imaging archive 304, or Picture Archiving and Communications System (PACS), and may export radiation planning files to reside on the PACS system. The PACS system may be a distributed system of storage devices that may be networked and be made accessible to the treatment planning system by, for example, networked connection.

The medical images in two-dimensional, three-dimensional volumetric, or four-dimensional format (temporal) with multiple contrast series and potentially acquired through multiple imaging modalities, may be transferred in whole, or in part (previously segmented anatomy or lesion) to the treatment planning system. In the treatment planning system 302 the user 306 may interface with the system, for example using a mouse, computer, touch screen or other such device, and may delineate critical structures, and treatment volume and anatomy of interest. Constraints on a treatment plan can be entered through a user interface.

In an additional embodiment, the treatment planning system 302 may communicate with a treatment planning database 308. The treatment planning database 308 may contain previous treatment templates that may facilitate computation of the therapy dose maps and treatment plans or may provide an initial estimate for the therapy dose maps and treatment plans. Additionally, specific information about the HDR system, or brachytherapy seeds, or catheters anticipated to be used in the treatment may be contained in the treatment planning database 308. This information may be used by the treatment planning system 302 to generate a specific dose plan.

In an additional embodiment, the treatment planning system 302 may communicate with an additional planning server 310. This server 310 may be used to accelerate the determination of a treatment plan by performing parallel calculations across multiple processors and networks. In alternative embodiments, many networks of processors may be used to facilitate calculations and processing. Additionally, processing on multiple processing elements on the treatment planning system, including, for example, the graphics card may accelerate determination of treatment plans. The information provided back to the treatment planning system 302 may be a part or the entire treatment plan. The systems, methods and computer programming presented in this disclosure may be adapted for to parallel processing to speed processing of the large number of equations. Multiple iterative approaches to refine the treatment plan are also possible, and could also benefit from systems adapted for parallel processing.

In an additional embodiment, the treatment planning system 302 may receive input from a device tracking 316 or similar system which may measure the position of catheters and seed applicators, mobilization grids and the anatomy of interest amongst other things. In a further embodiment an imaging system 314 may be used in-procedure to image the anatomy and tissue of interest as well as catheters, seeds and HDR applicators. This imaging system 314 may include MRI, CT, X-ray, Ultrasound or a combination thereof. This imaging and tracking information may be used in the treatment planning system 302 to perform an iterative calculation of dose and the treatment plan based on this updated information.

The treatment planning system 302, the associated system components and the methods and computer programming described herein, may determine the treatment plan and corresponding therapy dose map may operate iteratively, such that the user may approve or make iterative adjustments to continue to refine the treatment plan. The calculation of the dose plan in the manner proposed in this disclosure may be performed on the treatment planning system 302 in whole or in part in a parallel manner across the other components of the computing system disclosed.

As described above, treatment planning system 302 of FIG. 3 may be coupled to a guidance system (not shown) to assist and/or direct a treatment device to place one or more seeds at a determined location of seed placement according to a treatment plan. The guidance system can, based on data representing the tissue being treated, treatment plan and therapy dose map, the patient being treated and/or other data, provide guidance information to a display to guide a user's placement of a treatment device. In alternative embodiments, the guidance information can be provided to an automated and/or robotic device for positioning the treatment device.

For example, in some embodiments the treatment device can be a catheter and seeds, in which the catheter deposits brachytherapy seeds to a desired location according to the plan. In other therapies or treatments, the treatment device or seed being placed at determined therapy location(s) can be for other treatments, such as heat/cold, electro-therapy or ultrasonic devices.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for generating a treatment plan for therapy, comprising:
   obtaining image data representing a tissue;
   using a processor to:
   determine a therapy dose map comprising dose values for a plurality of dose points based on the image data;
   form a desired dose value vector comprising the dose values for the plurality of dose points;
   determine a one or more potential therapy locations based on the image data;
   determine a therapy dose map equation for each of the plurality of dose points based on the one or more potential therapy locations;
   form a matrix based on the therapy dose map equations for each dose point;
   determine an inverse of the matrix; and determine the treatment plan by multiplying the desired dose value vector by the inverse of the matrix.

2. The method of claim 1, wherein the treatment plan is a vector representing a one or more determined therapy locations.

3. The method of claim 2, wherein based on the treatment plan, one or more treatment devices, each corresponding to the one more determined therapy locations, are injected into the tissue to each determined therapy location.

4. The method of claim 2, wherein the treatment plan is for brachytherapy and the one or more treatment devices are each brachytherapy seeds.

5. The method of claim 4, wherein the resulting treatment plan vector represents the one or more determined brachytherapy seed locations multiplied by a dwell time associated with each determined brachytherapy seed location.

6. The method of claim 4, wherein the each therapy dose map equation is determined by summing dose values from the one or more potential therapy locations at each dose point.

7. The method of claim 6, wherein the matrix is an M×N matrix where M is equal to The number of dose points in the plurality of dose points and N is equal to the number of potential therapy locations.

8. The method of claim 4, wherein determining the brachytherapy treatment plan includes generation of a second therapy dose map from the one or more determined therapy locations.

9. The method of claim 8, wherein at least one of the one or more determined therapy locations or the dwell time associated with the each determined therapy location is adjusted to determine a further therapy dose map.

10. A computer media product, comprising a non-transitory computer usable medium having a computer readable code embodied therein, the computer readable code being readable by a computer processor of a computer system to cause the system to:
obtain image data representing a tissue;
determine a therapy dose map comprising dose values for a plurality of dose points based on the image data;
form a desired dose value vector comprising the dose values for the plurality of dose points;
determine a one or more potential therapy locations based on the image data;
determine a therapy dose map equation for each of the plurality of dose points based on the one or more potential therapy locations;
form a matrix based on the therapy dose map equations for each dose point;
determine an inverse of the matrix; and
determine the treatment plan by multiplying the desired dose value vector by the inverse of the matrix.

11. The computer media product of claim 10, wherein the treatment plan is a vector representing a one or more determined therapy locations.

12. The computer media product of claim 11, wherein based on the treatment plan, one or more treatment devices, each corresponding to the one more determined therapy locations, are injected into the tissue to each determined therapy location.

13. The computer media product of claim 11, wherein the treatment plan is for brachytherapy and the one or more treatment devices are each brachytherapy seeds.

14. The computer media product of claim 13, wherein the resulting treatment plan vector represents the one or more determined brachytherapy seed locations multiplied by a dwell time associated with the each determined seed location.

15. The computer media product of claim 13, wherein the each therapy dose map equation is determined by summing dose values from the one or more potential therapy locations at each dose point.

16. The computer media product of claim 15, wherein the matrix is an M×N matrix where M is equal to the number of dose points in the plurality of dose points and N is equal to the number of potential therapy locations.

17. The computer media product of claim 13, wherein determining the brachytherapy treatment plan includes generation of a second therapy dose map from the one or more determined brachytherapy seed locations.

18. The computer media product of claim 17, wherein at least one of the one or more determined therapy locations or the dwell time associated with the each determined therapy location is adjusted to determine a further therapy dose map.

19. A plan generation system for generating a treatment plan comprising:
a medical image storage medium for storing imaging data;
a treatment planning storage medium for storing treatment planning data;
a treatment planning system in communication with the medical image storage medium and treatment planning storage medium, the planning system obtaining the imaging data from the medical image storage medium and obtaining the treatment planning data from the treatment planning storage medium for analysis by a processor of the planning system, the processor:
determining a therapy dose map comprising dose values for a plurality of dose points based on the imaging data received from the medical image storage medium,
forming a desired dose value vector comprising the dose values for the plurality of dose points,
determining a one or more potential therapy locations based on the image data received from the medical image storage medium,
determining a therapy dose map equation for each of the plurality of dose points based on the one or more potential therapy locations,
forming a matrix based on the therapy dose map equations for each dose point,
determining an inverse of the matrix,
determining the treatment plan by multiplying the desired dose value vector by the inverse of the matrix;
displaying the treatment plan to a display device to guide a user in injecting one or more treatment devices, each corresponding to the one more determined therapy locations, into the tissue to the each therapy location based on the treatment plan.

20. The plan generation system claim 19, wherein:
the treatment plan is a vector representing one or more determined therapy locations multiplied by a dwell time associated with each determined therapy location;
each therapy dose map equation is determined by summing dose values from the one or more potential therapy locations at each dose point; and
the matrix is an M×N matrix where M is equal to the number of dose points in the plurality of dose points and N is equal to the number of potential therapy locations.

21. The plan generation system claim 20, wherein the treatment device is a brachytherapy seed.

* * * * *